United States Patent [19]

Tsien et al.

[11] Patent Number: 4,806,604
[45] Date of Patent: Feb. 21, 1989

[54] PHOTOSENSITIVE CALCIUM CHELATORS

[75] Inventors: Roger Yonchien Tsien, Berkeley; Stephen R. Adams, Walnut Creek, both of Calif.

[73] Assignee: Regents of the University of California, Berkeley, Calif.

[21] Appl. No.: 49,658

[22] Filed: May 13, 1987

[51] Int. Cl.$^4$ ............... C07D 407/02; C07D 317/48; C07D 307/20; C07D 309/10; C07D 207/12; C07D 211/40; C07D 333/32; C07D 335/02

[52] U.S. Cl. ...................... 549/439; 549/6; 549/7; 549/8; 549/9; 549/11; 549/21; 549/28; 549/60; 549/65; 549/222; 549/346; 549/362; 549/435; 549/437; 562/435; 560/21; 560/129; 560/251; 548/413; 548/526; 548/544; 548/545; 546/24; 546/197; 546/220; 540/596; 540/604; 558/47; 558/48; 558/158; 558/193

[58] Field of Search ............... 562/435; 560/21, 155, 560/251, 227; 558/48, 193, 47, 162, 158; 549/435, 437, 439, 362, 449, 417, 346, 9, 11, 28, 60, 65, 220, 222, 6, 7, 8, 21; 548/544, 545, 413, 526, 541; 546/24, 197, 220; 540/596, 604

[56] References Cited

U.S. PATENT DOCUMENTS 4,603,209 7/1986 Tsien et al. ................ 548/236
4,689,432 8/1987 Tsien et al. ................ 562/435

OTHER PUBLICATIONS

Gurney, et al., "Activation of a Potassium Current by Rapid Photochemically Generated Step Increases of Intracellular Calcium in Rat Sympathetic Neurons"-Proc. Natl. Acad. Sci. USA, vol. 84, pp. 3496-3500, May 1987.
Gurney, et al., "Light-Flash Physiology with Synthetic Photosensitive Compounds", Physiol. Rev., 67 (2): 583-617 (1987).
Tsien, Biochemistry, 19: 2396-2404 (1980).

Primary Examiner—John W. Rollins
Assistant Examiner—W. Catchpole
Attorney, Agent, or Firm—Fitch, Even, Tabin & Flannery

[57] ABSTRACT

The present invention discloses a new class of calcium chelating compounds which have a decreased affinity for calcium following illumination. These new compounds contain a photolabile nitrobenzyl derivative coupled to a tetracarboxylate $Ca^{2+}$ chelating parent compound having the octacoordinate chelating groups characteristic of EGTA or BAPTA. However unlike EGTA or BAPTA-like compounds, in which the two halves of the chelator are linked by a simple 1,2-ethanediyl moiety, the compounds of the present invention modify the stereochemical conformation of this linkage by adding bulky substituents or incorporating the linkage into a carbocyclic or heterocyclic ring. In a first form, the new compounds are comprised of a BAPTA-like chelator coupled to a single 2-nitrobenzyl derivative, which in turn is a photochemical precursor of a 2-nitrosobenzophenone. In a second form, the new compounds are comprised of a BAPTA-like chelator coupled to two 2-nitrobenzyl derivatives, themselves photochemical precursors of the related 2-nitrosobenzophenones.

8 Claims, 2 Drawing Sheets

PHOTOSENSITIVE CALCIUM CHELATORS

This invention was made with government support under Grant No. EY-04372 with the National Institutes of Health and the University of California. The government has certain rights in this invention.

FIELD OF THE INVENTION

The present invention relates to photolabile calcium 2+ chelators whose affinity for calcium is decreased by illumination.

BACKGROUND OF THE INVENTION

Although $Ca^{2+}$ is a well-established intracellular messenger, there are still many unanswered questions concerning the kinetics and spatial localization of its effects. As a means of supplying the data needed to answer some of these questions, chelators whose affinity for calcium is decreased by illunination, such as those disclosed in U.S. Pat. No. 4,689,432, are now being used to induce fluctuations in free calcium levels similar to those which occur in vivo. Also see, Gurney and Lester (1987).

Although the photolabile chelator compounds disclosed in U.S. Pat. No. 4,689,432 are useful for examining some processes which involve calcium, unfortunately the calcium 2+ affinity of some of these compounds is not strong enough for studying others. For example, with chelators such as nitr-2, a compound disclosed in U.S. Pat. No. 4,689,432, at values of cytosolic free calcium 2+ typical for resting cells, only about ½ or less of the uphotolyzed chelator molecules bear calcium 2+ ions. Obviously the less calcium 2+ ions that are bound over to the chelator, the less that can be released by photolysis. In addition, those molecules which escape photolysis during the light flash tend to buffer the free calcium rise generated by those molecules which do photolyse.

The present invention discloses a new class photolabile calcium chelator compounds. Unlike the calcium chelators disclosed in U.S. Ser. No. 648,536, in which the two halves of the chelator are linked by a simple 1,2-ethanediyl (—$CH_2CH_2$—) moiety, the compounds of the present invention modify the stereochemical conformation of this linkage by adding bulky substituents or incorporating the linkage into a carbocyclic or heterocyclic ring. Such stereochemical modifications can decrease the $Ca^{2+}$ affinity 75-fold or increase its 4-fold compared to prior art compounds. The new compounds also release $Ca^{2+}$ more rapidly after photolysis than do compounds of the prior art such as nitr-2. These differences make the compounds of the present invention especially useful for studying the effects of $Ca^{2+}$ on such phenomena as ion-channel gating and muscle contraction.

SUMMARY OF THE DRAWINGS

In the chart, reagents which were bought or prepared by known standard procedures are identified with Arabic numbers within brackets. Newly synthesized compounds are identified with Roman numerals and lower case letters such as a, b, c, etc. In this notation, a means containing a cis-cyclopentanediyl linkage; b means containing a trans-cyclopentanediyl linkage; c means containing a cis-cyclohexanediyl linkage; d means containing a trans-cyclohexanediyl linkage; e means containing a cis-2,3-butanediyl linkage; f means containing a trans-2,3-butanediyl linkage; and g means containing a cis-3,4-tetrahydrofurandiyl linkage.

DEFINITION OF TERMS USED HEREIN

The new photolabile $Ca^{2+}$ chelators disclosed herein are named with hyphens to distinguish the number 1 from the letter 1, e.g., nitr-7.

As used herein, nitr-7 means cis-1-(2-bis(carboxymethyl)amino-5-(1-hydroxy-1-(2-nitro-4,5-methylenedioxyphenyl)methyl)phenoxy)-2-(2-bis(carboxymethyl)amino-5-methylphenoxy)cyclopentane. In the flow chart of FIG. 1, nitr-7 is shown as compound VIIa.

As used herein, TMS triflate or TMS-OTf means trimethylsilyl trifluoromethanesulfonate.

As used herein, MOPS means 3-(N-morpholino)propanesulfonic acid.

As used herein, EGTA means ethylene glycol bis(beta-aminoethyl ether)-N,N,N',N'-tetracetic acid.

As used herein, BAPTA means 1,2-bis(2-aminophenoxy)ethane N,N,N'N'-tetraacetic acid; the chemical structure for BAPTA is:

As used herein, quin1 means 2-[[2-[bis(carbxymethyl)amino]-5-methylphenoxy]methyl]-8-[bis(carboxymethyl)amino]-quinoline.

As used herein, quin2 means 2-[[2-[bis(carboxymethyl)amino]-5-methylphenoxy]-methyl]-6-methoxy-8-[bis(carboxymethyl)amino]-quinoline; the chemical structure for quin2 is:

As used herein, BAPTA-like means substituted derivatives of BAPTA which retain the essential characteristic of two bis(carboxymethyl)amino-substituted phenyl rings, said rings being linked at the positions ortho to the amines through a four atom bridge wherein the atom adjacent to each phenyl ring is N or O and the two center atoms are each C. By this definition, it is meant that "BAPTA-like" includes compounds like quin-1 and quin-2.

As used herein, pharmaceutically acceptable esters mean those readily hydrolyzable esters which are known and used in the pharmaceutical industry, especially alpha-acyloxyalkyl esters.

As used herein, pharmaceutically acceptable nontoxic salts mean carboxylic acid salts wherein the counterion or ions are all Na, K, $NR_4+$ (where R=H, $C_1$-$C_4$ alkyl or a mixture thereof), choline, N-methylglucamine, Ca, or Mg, or some combination of these counterions, or some combination of acid salts or these counterions plus free acid groups.

As used heren, microM means micromolar.

Temperatures herein are given in degrees Centigrade.

REFERENCE LIST

Publications

The scientific publications cited herein are expressly incorporated by reference.
1. Gurney, A. M. and Lester, H. A., (1987) "Light-Flash Physiology with Synthetic Photosensitive Compounds", *Physiol. Rev.* 67(2): 583–617.
2. Gurney, A. M., Tsien, R. Y., and Lester, H. A., (1987) "Activation of a potassium current by rapid photochemically generated step increases of intracellular calcium in rat sympathetic neurons", *Proc. Natl. Acad. Sci., USA,* 84: (in press).
3. March, J., (1977) *Advanced Organic Chemistry,* Second Edition, McGraw Hill at pp. 498–499.
4. Martell, A. E. and Smith, R. M., (1974) *Critical Stability Constants,* Vol. 1, Plenum Press, NY.
5. Noyori, R., Murata, S. and Suzuki, M., (1981) *Tetrahedron* 37: 3899–3910.
6. Tsien, R. Y., (1980) *Biochemistry* 19: 2396–2404.

Patents

1. Tsien, et al., U.S. Pat. No. 4,689,432, issued Aug. 25, 1987.

DESCRIPTION OF THE INVENTION

BRIEF DESCRIPTION OF THE INVENTION

The present invention comprises a new class of compounds, which when illuminated, change their affinity for calcium. The compounds contain a photolabile nitrobenzyl derivative coupled to a tetracarbxylate parent compound having the octa coordinate chelating groups characteristic of EGTA of BAPTA. However unlike EGTA or BAPTA-like compounds, in which the two halves of the chelator are linked by a simple 1,2-ethanediyl (—$CH_2CH_2$—) moiety, the compounds of the present invention modify the stererochemical conformation of this linkage by adding bulky substituents or incorporating the linkage into a carbocyclic or heterocyclic ring. Such stereochemical modifications can decrease the $Ca^{2+}$ affinity 75-fold or increase it 4-fold compared to prior art compounds. The new class of calcium chelators disclosed herein also differ from prior art compounds in the time they take to release calcium in response to flash illumination. This makes the compounds of the present invention especially useful for studying physiological processes such as ion-channel gating and muscle contraction. The new chelators are also useful, in combination with prior art chelators, for studying various physiological processes by comparing the effects induced by different chelators. See generally Gurney, et al. (1987) and Gurney and Lester (1987).

In a first form, the new compunds are comprised of a BAPTA-like chelator, in which the two halves of the chelator are linked by a linkage selected from the group comprised of: (a) a simple 1,2-ethanediyl (—$CH_2CH_2$—) moiety having bulky substituents such as —$CH_3$—, —$C_2H_5$, or —$CH_2OH$ added thereto, (b) a 1,2-ethanediyl moiety incorporated into a carbocyclic ring and, (c) a 1,2-ethanediyl moiety incorporated into a heterocyclic ring; wherein the chelator is coupled to a single 2-nitrobenzyl derivative, which in turn is a photochemical precursor of a 2-nitrosobenzophenone. In this form the new compounds are comprised of a chemical compound having the generic formula:

and the pharmaceutically acceptable nontoxic salts and esters thereof wherein:

A is —$NO_2$ or —H;

$R^1$ is selected from the group comprised of —H (unless $R^2$ is also H), —$CH_3$, —F, —Cl, and —Br;

$R^2$ is selected from the group comprised of —H (unless $R^1$ is also H), —$CH_3$, —F, —Cl, —Br, and $C_1$-$C_4$ alkoxy;

$R^3$, $R^4$ and $R^5$ are independently —H, OH, $NR^6R^7$, or alkoxy, or $R^3$ and $R^4$ together are —$OCH_2O$— or —$OCH_2CH_2O$— and $R^5$ is —H, OH, $NR^6R^7$, or alkoxy, or $R^4$ and $R^5$ together are —$OCH_2O$— or —$OCH_2CH_2O$— and $R^3$ is —H, OH, $NR^6R^7$, or alkoxy;

X is selected from the group comprised of —OH, alkoxy, —Cl, —Br, —$NR^6R^7$, —$OCOCH_3$, —OCOCF$_3$, —$OCOCH_2NH_2$, —$OPO_3H$, and —$OSO_2CH_3$;

$R^6$ and $R^7$ are independently —H, methyl or ethyl;

$R^8$ and $R^9$ are independently —H, —$CH_3$, —$C_2H_5$, or —$CH_2OH$ except that both may not be —H simultaneously; or $R^8$ and $R^9$ together are —$(CH_2)_m$—Y—$(CH_2)_n$— where m and n are independently 1 or 2 and Y is selected from the group comprised of —$CH_2$—, —O—, —$NR^6$—, —S—, and —S—S—; and W is —H, —OH, or —$NHR^6$.

In a second form, the new compounds are comprised of a BAPTA-like chelator, in which the two halves of the chelator are linked by a linkage selected from the group comprised of: (a) a simple 1,2-ethanediyl (—$CH_2CH_2$—) moiety having bulky substituents such as —$CH_3$—, —$C_2H_5$, or —$CH_2OH$ added thereto, (b) a 1,2-ethanediyl moiety incorporated into a carbocyclic ring and, (c) a 1,2-ethanediyl moiety incorporated into a heterocyclic ring; wherein the chelator is coupled to two 2-nitrobenzyl derivatives, themselves photochemical precursors of the related 2-nitrosobenzophenones. In this form, the new compounds are comprised of a chemical compound having the generic formula:

and the pharmaceutically acceptable non-toxic salts and esters thereof wherein:

A is —$NO_2$ or —H;

$R^3$, $R^4$ and $R^5$ are independently —H, OH, $NR^6R^7$, or alkoxy, or $R^3$ and $R^4$ together are —$OCH_2O$— or —$OCH_2CH_2O$— and $R^5$ is —H, OH, $NR^6R^7$, or alkoxy, or $R^4$ and $R^5$ together are —$OCH_2O$— or —$OCH_2CH_2O$— and $R^3$ is —H, OH, $NR^6R^7$, or alkoxy;

X is selected from the group comprised of —OH, alkoxy, —Cl, —Br, —$NR^6R^7$, —$OCOCH_3$, —$OCOCF_3$, —$OCOCH_2NH_2$, —$OPO_3H$, and —$OSO_2CH_3$;

$R^6$ and $R^7$ are independently —H, methyl or ethyl;

$R^8$ and $R^9$ are independently —H or —$CH_3$ or —$C_2H_5$ or —$CH_2OH$ except that both may not be —H simultaneously; or $R^8$ and $R^9$ together are —$(CH_2)_m$—Y—$(CH_2)_n$— where m and n are independently 1 or 2 and Y is selected from the group comprised of —$CH_2$—, —O—, —$NR^6$—, —S—, and —S—S—; and W is —H, —OH, or —$NHR^6$.

DETAILED DESCRIPTION OF THE INVENTION

The present invention comprises a new class of photosensitive calcium chelating compounds which decrease their affinity for calcium when exposed to light. Generic formulas for these photolabile compounds are given above. Compounds of the type disclosed and claimed herein consist of a calcium 2+ chelating portion containing two 2-bis(carboxymethyl)aminophenoxy groups linked through a 1,2-propanediyl or 2,3-butanediyl or a 1,2-cycloalkanediyl or through two adjacent carbon atoms in a heterocyclic ring, for example a 3,4-tetrahydrofurandiyl, and a nitroaryl portion linked to the chelating portion by a substituted methylene bridge.

Figure 1:
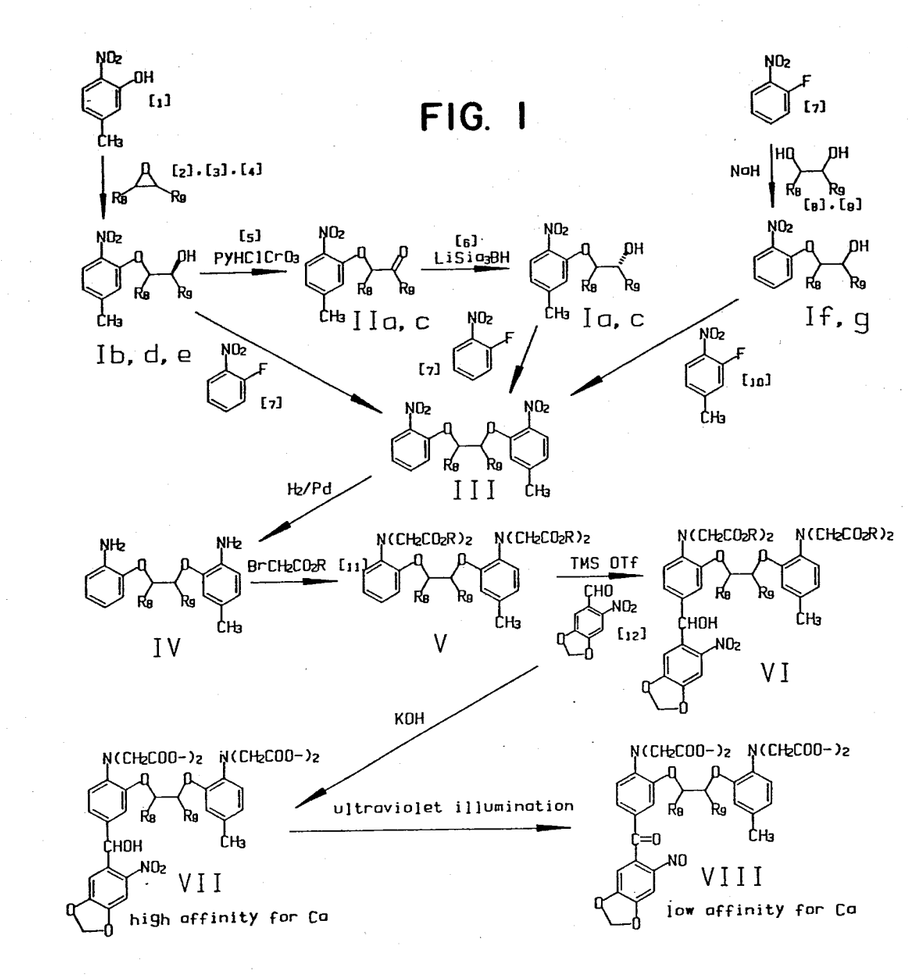
FIG. 1 is a flow chart illustrating synthesis of chelators of the present invention.

The synthesis of the new photolabile compounds claimed herein is illustrated in the detailed synthesis of nitr-7 (See FIG. 1). Those skilled in the art will recognize that other new forms of these photolabile $Ca^{2+}$ chelators can be prepared by using related synthetic methods and starting materials.

Full descriptions of the reaction conditions are described below. In both FIG. 1 and the discussion that follows, numerals, both Roman and Arabic, and lower case letters are sometimes used as a shorthand means of identifying the various chemical compounds. Reagents used but not synthesized are labeled on the flow chart in FIG. 1 with bracketed Arabic numerals. In the synthesis section that follows, these reagents are identified with bracketed Arabic numbers.

Preparations of calcium chelating compounds suitable for use as intermediates in this invention have been described (see Tsien, 1980). In addition to the compounds described therein, those skilled in the art will realize that by using standard techniques it is possible to prepare derivatives of said compounds contaning various $R^1$, $R^2$, and W groups (see generic formulas in Brief Description of the Invention section, supra). Such derivatives are within the scope of the present invention.

The nitrophenyl portion of the new compounds comes from a suitable 2-nitro-benzaldehyde or 2,6-dinitrobenzaldehyde. In preferred synthesis methods, the aldehyde is used directly to prepare the compounds.

The various R and W substituents allow a number of related compounds to be prepared. When W is —OH, —alkoxy, or —$NHR^6$, the heteroatom may exert electronic and steric effects to modify the stability of the photoactive transition state. $R^1$ and $R^2$ can be altered to modify the $K_d$ of the chelator portion of the molecule, and to control the electrophilic aromatic substitution of the nitrobenzaldehyde derivative so that one or two photolabile groups are incorporated in the final molecule. $R^3$ through $R^5$ substituents will influence the electron density of the nitrophenyl ring and therefore can influence the wavelength needed to activate the photo reaction.

The key step in preparing compounds of the type disclosed and claimed herein is the condensation of a 2-nitrobenzaldehyde with an aromatic, BAPTA-like chelator. The obvious, textbook methods for synthesizing benzhydrols either failed or were unsuitable because of the many other substituents on the desired molecule. For example, the classic methods for condensing aromatic rings with aldehydes or ketones ("hyroxyalkylation", see March, 1977) are known not to stop at the benzhydrol stage but to go on to triarylmethanes. Also conventional Lewis acids needed to activate the aldehyde would deactivate the BAPTA-like substrates because of their amino functionality. Therefore we used the selective Lewis acid, trimethylsilyl trifluoromethane sulfonate (see Noyori, et al., 1982), to carry out the required electrophilic aromatic substitution. The method can be practiced by mixing together one equivalent of an aryl compound and a hindered, tertiary amine, then adding TMS-triflate, and finally adding a 2-nitroaryl aldehyde or dialkyl acetal thereof.

In the preparation of compounds of the invention that contain only one photolabile nitrobenzyl group, if $R^2$ is anything except hydrogen, the 5 position of that ring will be blocked and nitrobenzylation can proceed only at the desired 5 position of the 4-W-phenyl ring or equivalent quinoline or benzopyran. If $R^2$ is hydrogen, the presence of halogen at $R^1$ will deactivate that ring for electrophilic substitution and nitrobenzylation will occur mainly at the desired position. Products of the first type where $R^2$=H and $R^1$=H or alkyl can be prepared only by controlled nitrobenzylation and separation of the desired product, so preparation of such compounds is not recommended.

To prepare compounds containing two nitrobenzyl groups, $R^2$ must be hydrogen and $R^1$ can be hydrogen, alkyl or any form appropriate for substituent W. In this case, the desired nitrobenzylation occurs at the 5 position of both phenyl rings or the 5 position of both the $R^1$, $R^2$ phenyl and of the quinoline.

It is known that cation affinities of BAPTA derivatives can be increased or decreased by appropriate electron-donating or electron-withdrawing substituents on the benzene rings (see generally Tsien, 1980). For example, substitution of two methyl groups for the two hydrogens para to the two nitrogens of BAPTA strengthened $Ca^{2+}$ binding by 0.4 log unit and similar disubstitution with bromine weakened $Ca^{2+}$ binding by 1.2 log units (see generally, Tsien, 1980). We have found that monosubstitution gives half as much effect on calcium affinity (data not shown). Those skilled in the art will realize that the effect of other substituents on the cation affinities of the present compounds should be quantitatively predictable by a Hammett-type linear free-energy relation.

It is also known that the greatest change in chelating characteristics occurs within 2 log $[Ca^{2+}]$ units of the $K_d$ of any particular chelator (see Tsien, 1980). As a result, it would be helpful to have chelators available which have a range of $K_d$'s. To this end, $R^1$ and $R^2$ can be varied to adjust the $K_d$ up or down. As expected, the nitrobenzyl component of the molecule weakens $Ca^{2+}$ binding by 0-0.3 log units (compare $K_d=160$ nM with BAPTA $K_d=100$ nM, (see Tsien, 1980).

The photolabile compounds disclosed and claimed herein can also be esterified using an alpha-alkyloxyalkyl bromide. Such esters are hydrophobic enough to readily cross cell membranes, but once within the cell are cleaved by cytosolic esterases to regenerate the free acids.

Methods for synthesizing the new photolabile $Ca^{2+}$ chelators disclosed herein are outlined in the following Compound Synthesis section.

Compound Synthesis

Most reagents and solvents used in the syntheses were ACS or HPLC grade, and used as received from Aldrich, Mallinkradt, Fisher, or J. T. Baker unless otherwise stated. Dry dimethylformamide (DMF) was obtained from Aldrich, Gold Label, stored over 4A molecular sieves and used as received. Dimethoxyethane was dried over sodium-lead alloy. $CH_2Cl_2$ and $CHCl_3$ were redistilled from $P_2O_5$; tetrahydrofuran (THF) was redistilled from $CaH_2$. In testing the various reaction products, proton magnetic resonance were recorded on a Varian EM-390 90 MHz spectrometer in $CDCL_3$ unless otherwise noted. Peaks are reported below in the following format: NMR (solvent, operating frequency): chemical shift in ppm from tetramethylsilane, multiplicity (s=singlet, d=doublet, t=triplet, q=quartet, m=multilet, br=broad), spin-spin coupling constant if appropriate, integrated number of protons. Sometimes several adjacent peaks are too close for their integrals to be separated, in which case only the total integral for a cluster is stated.

UV absorbance spectra were recorded on a Cary 210 or a Perkin Elmer Lambda Array 3840 spectrophotometer at $22\pm2°$ C. Melting points are uncorrected and elemetal analysis were performed by the Microanalytical Laboratory in the Department of Chemistry at the University of California Berkeley.

Thin-layer chromatography (TLC) was carried out on precoated silica gel (60F-254, E. Merck) or reverse phase (RP-18 F-254s, E. Merck) plates. For column chromatography, silica gel 60(230–400 mesh, E. Merck) was used. Since all 2-nitrobenzaldehyde and 2-nitrobenzyl alcohol derivatives are sensitive to near ultraviolet light, handlings were performed under an orange safety lamp.

Those skilled in the art will realize that starting from esters such as (VI) or acids (VII) where X=OH (see generic formula in Brief Description of the Invention section), analogs containing X=—OCOCH$_3$, —OCOCF$_3$, —O—glycyl, —OPO$_3$H, —OSO$_2$CH$_3$ could be readily prepared by acylation, phosphorylation, or methanesulfonylation under standard conditions. Also starting from esters where X=OH, analogs with X=Cl or Br could be prepared using SOCl$_2$ or PCl$_3$ or PBr$_3$ or other standard means for converting alcohols to halides. Esters with X=NR$^6$R$^7$ could be prepared from esters with X=Br or X=OSO$_2$CH$_3$ by nucleophilic substitution under standard conditions.

COMPOUND Ib

Trans-2'(5-methyl-2-nitrophenoxy) cyclopentanol was prepared as follows:

Cyclopentene oxide [reagent 2] (8.73 mL, 0.1 mol), 5-methyl-2-nitrophenol (15.3 g, 0.1 mol) [reagent 1] and potassium 5-methyl-2-nitrophenoxide (1.91 g, 0.01 mol) were dissolved in dry DMF (5 mL) and refluxed for 20 h. under argon. The cooled reaction mixture was diluted with aq. NaOH solution (100 mL 1M) and extracted with toluene (three 50 mL portions). The combined extracts were washed with $H_2O$ (3×50 mL), dried (Na$_2$SO$_4$), toluene removed by evaporation and the product [compound Ib] collected to give 17.0 g (72%) of an orange oil which crystallized on cooling. M.p 42°–44°.

$^1$H NMR delta 1.9(br m, 6H, cyclopentyl—CH$_2$—), 2.40 (s, 3H, CH$_3$), 4.40 (br m, 1H, —CH—OH) 4.65 (m, 1H, —CH—OAr) 6.80(d, 1H, J=8 Hz, H-64) 6.93 (s, 1H, H-6) 7.67 (d, 1h, J=8 hz, H-3).

COMPOUND Id

Compound Id was synthetsized by the same method as Ib but using cyclohexene oxide [reagent 3] instead of cyclopentene oxide. Recrystallizaton from hexane gave yellow crystals, yield 56%. M.p. 55°–57°. $^1$H NMR delta 1.50, 1.78, 2.1 (br. m, 8H, cyclohexyl) 2.40 (s, 3H, CH$_3$), 3.30 (s, br, 1H, OH), 3.73 (m, 1H, —CH—OH), 4.05 (m, 1H, —CH—OAr), 6.78 (d, 1H, J=8 Hz, H-4) 6.90 (s, 1H, H-6) 7.67 (d, 1H, J=8 Hz, H-3).

COMPOUND Ie

Compound Ie was synthetsized by the same method as Ib but using trans-2,3-epoxybutane [reagent 4] instead of cyclopentene oxide. The resulting oil (16% yield of Ie) was used without further purification.

$^1$H NMR delta 1.20, 1.30 (2d, 6H, J=5 Hz, butylCH$_3$) 2.40 (s, 3H, Ar—CH$_3$), 2.72 (s, 1H, —OH), 4.00, 4.53 (2m, 2h, J=3 Hz, —CH—), 6.85 (d, 2H J=8 Hz H-4) 6.95 (s, 1H, H-6) 7.80 (d, 2H, J=8 Hz H-3).

COMPOUND IIa

2'-(5-methyl-2-nitrophenoxy) cyclopentanone was prepared as follows:

Compound Ib (8.3 g, 35 mmol) dissolved in CH$_2$Cl$_2$ (10 mL) was added in one portion to a stirred suspension of pyridinium chlorochromate [reagent 5] (11.3 g, 55 mmol) in CH$_2$Cl$_2$ (70 ml) and stirred at room temperature for 16 h. The reaction mixture was diluted with Et$_2$O (350 mL) and decanted from the dark tar which was washed (3×50 mL) with Et$_2$O. The combined extracts were filtered through Celite and evaporated to dryness to yield an oil which crystallized. Recrystallization from MeOH gave IIa as yellow crystals (6.60 g, 80%) M.p 65°–66°.

$^1$H NMR delta 2.10 (m, 6H, —(CH$_2$)$_3$—), 2.33 (s, 3H, CH$_3$), 4.63 (t, 1H, CH), 6.80 (d, 1H J=8 Hz, H-4) 7.02 (s, 1H, H-6) 7.70 (d, 2H J=8 Hz, H-3)

COMPOUND IIc

Oxidation of the cyclohexanol derivative Id required a six-fold excess of pyridinium chlorochromate and a reaction time of 5 days to give compound IIc (88% yield) as a yellow solid, recrystallized from isopropyl ether. M.p. 125°–8°.

$^1$H NMR delta 1.6–2.6 (m's, 8H, —(CH$_2$)$_4$—) 2.33 (s, 3H, CH$_3$) 4.63 (t, 1H, CH) 6.80 (d, 1H, J=8 Hz H-4) 7.02 (s, 1H, H-6) 7.73 (d, 2H, J=8 Hz, H-3).

COMPOUND Ia

IIa (5.86 g, 25 mmol) dissolved in dry THF (25 mL) at −10° C. was added dropwise with stirring to a solution of lithium trisiamylborohydride [reagent 6] (30 mmol) in THF (30 ml) at −78° C. under a N$_2$ atmosphere. After 2 h, the red reaction mixture was allowed to warm up to room temperature (1 h), quenched with H$_2$O (4 mL) and EtOH (15 mL), made alkaline with aqueous KOH (6 mL, 10M), and oxidized by cautious addition of 30% aq. H$_2$O$_2$ (15 mL) with cooling. After saturating with K$_2$CO$_3$, the aqueous layer was separated and washed with Et$_2$O:THF (1:1, 2×10 mL). The combined organic extracts were dried (MgSO$_4$), evaporated to dryness, and the product distilled bulb-to-bulb at 180°–200° C. at 0.1 mm Hg to yield Ia as an orange oil (4.55 g, 77%).

$^1$H NMR delta 1.9 (br m, 6H, —(CH$_2$)$_3$—) 2.40 (s, 3H, CH$_3$) 3.05 (br s, 1H, OH), 4.20, 4.66 (2m, 2H, CH) 6.82 (d, 1H, J=8 Hz, H-4), 6.90 (s, 1H, H-6) 7.76 (d, 1H, J=8 Hz, H-3).

TLC in a system which separated the cis and trans-isomers Ia and Ib respectively, indicated complete conversion to the cis-isomer.

COMPOUND Ic

In analogy to the above preparation of Ia, IIc was reduced to Ic, a dark orange oil (54% yield) after chromatography on SiO$_2$ in ethyl acetate-hexane. $^1$H NMR delta 1.68 (br m's, 8H, —(CH$_2$)$_4$—), 2.40 (s, 3H, CH$_3$), 2.70 (br d, 1H, OH), 3.83 (br m, 1H, CH—), 4.53 (m, 1H, CH—OAr), 6.80 (d, 1h J=8 Hz H-49, 6.90 (s, 1H, H-6) 7.76 (d, 1H, J=8 Hz H-3).

COMPOUND Ig

Cis-3'-(2-nitrophenoxy)tetrahydrofuran-4'-ol (XIIh) was prepared as follows:

NaH (42 mg 57% suspension in oil, 1 mmol) was added portionwise with stirring to a solution of cis-tetrahydrofuran-3,4-diol [reagent 8] (0.21 g, 2 mmol) and 2-fluoronitrobenzene [reagent 7] (105 microL, 1 mmol) in dry DMF (1 mL). Thirty minutes after the final addition, the reaction mixture was diluted with H$_2$O (15 mL) and cooled on ice for at least 30 min. The solid precipitate of the diarylated byproduct was filtered off, the filtrate extracted with toluene (3×5 mL) and combined extracts dried (Na$_2$SO$_4$), and evaporated to dryness to yield the product, (Ig) as a yellow oil that crystallized on trituration with isopropyl ether, yield 111 mg. M.p. 59°–61°. TLC (5% MeOH-CHCl$_3$) showed less than 5% disubstituted by-product. The product was used without further purification.

1H NMR delta 3.13 (d, 1H, OH) 3.4–4.2 (m's, 4H, —CH$_2$OCH$_2$—), 4.45, 5.80 (2m, 2H, CH) 6.90–8.0 (m, 4H, aromatic).

COMPOUND If

Similarly to the preparation of compound Ig, addition of NaH (4 mmol) to a solution of (R,R)-(−)-2,3-butanediol [reagent 9] (5 mmol) and 2-fluoronitrobenzene [reagent 7] (4 mmol) in dry N-methylpyrrolidinone (2.5 mL), quenching with H$_2$O after 30 min., and extraction into ethyl acetate gave a mixture of the mono and di-substituted products which were separated on SiO$_2$ by eluting with ethylacetate-hexane to give a yellow oil, If (45%) and white solid (14%) respectively.

COMPOUND IIIa

Cis-1-(5'-methyl-2'-nitrophenoxy)-2-(2''-nitrophenoxy)cyclopentane was prepared as follows:

NaH (1.05 g, 57% oil suspension, 25 mmol) was added portionwise with stirring and cooling to a solution of Ia (4.27 g, 18 mmol) and 2-fluoronitrobenzene [reagent 7] (2.11 mL, 20 mmol) in dry 1,2-dimethoxyethane (25 mL). After standing at room temperature for 1 h, the reaction mixture was diluted with H$_2$O (100 mL) and extracted with CHCl$_3$ (3×50 mL); the extracts dried and evaporated to dryness to yield the crude product IIIa as an oil which crystallized on chilling. Recrystallization from acetone-methanol gave yellow crystals, m.p. 109°–111° yield, 4.8 g (74%).

$^1$H NMR delta 1.7–2.2 (m, 6H, —(CH$_2$)$_3$—), 2.35 (s, 3H, CH$_3$) 4.87 (m, 2H, CH), 6.7–7.8 (m's, 7H, aromatic).

COMPOUNDS III b, c, d and e

Compounds IIIb, IIIc, IIId and IIIe were synthesized from the corresponding alcohols by the same method used to synthesize compound Ia. The yield, physical and spectral properties were as follows:

IIIb: Orange oil, distilled bulb-to-bulb 230° C. at 0.25 mm Hg (63%)

$^1$H NMR delta 16–2.1 (m, 6H, —(CH$_2$)$_3$—), 2.40 (s, 3H, CH$_3$), 4.75 (m, 2H, CH), 6.8–7.8 (m, 7H, aromatic).

IIIc: Brown oil (SiO$_2$ chromatography, Ethylacetate-hexane) yield 74%

$^1$H NMR delta 1.3–22 (m's, 8H, —(CH$_2$)$_4$—), 2.37 (s, 3H, CH$_3$), 4.70 (br d, 2H, CH), 6.8–7.8 (m's, 7H aromatic).

IIId: Yellow crystals M.p. 86°–90° (60%)

$^1$H NMR delta 1.3–2.2 (m's, 8H, —(CH$_2$)$_4$—), 2.40 (s, 3H, CH$_3$) 4.63 (m, 2H, CH), 6.8–7.8 (m's, 7H, aromatic).

IIIe: Pale yellow solid M.p. 86° (64%) purified by SiO$_2$ chromatography.

$^1$H NMR delta 1.47 (d, 6H, J=6.5 Hz, CH$_3$) 2.42 (s, 3H, Ar—CH$_3$), 4.75 (q, d, 2H J=6.5, 3Hz, CH) 6.8–8.0 (m, 7H, aromatic).

COMPOUNDS IIIf and g

As in the synthesis of compounds IIIb, c, d and e, compounds IIIf and IIIg were similarly prepared from alcohols If and Ig respectively, but substituting 3-fluoro-4-nitrotoluene [reagent 10] for 2-fluoronitrobenzene. IIIf was an orange oil, separated by SiO$_2$ chromatography (ethyl acetate-hexane) yield 45%.

$^1$H NMR delta 1.33 (d, 6H, J=6.5 Hz, CH$_3$) 2.40 (s, 3H, Ar-CH$_3$) 4.75 (m, 1H, CH) 6.7–7.8 (m's, 7H, aromatic).

IIIg was obtained as a pale yellow precipitate on quenching the reaction mixture followed by recrystallization from ethanol. Yield 63% M.p. 145°–148°.

$^1$H NMR delta 2.37 (s, 3H, CH$_3$), 4.21 (m, 4H, —CH$_2$OCH$_2$—), 5.07 (m, 2H, CH) 6.8–7.8 (m's, 7H, aromatic).

COMPOUND IVa

Cis-1-(2'-amino-5'-methylphenoxy)-2-(2'''-aminophenoxy)cyclopentane was prepared as follows: IIIa (2.0 g, 5.58 mmol) was catalytically hydrogenated at room temperature and pressure with 200 mg 5% Pd/C in ethylacetate: 95% aq. EtOH (2:1). Uptake was complete within 1 h and after a further 1 h, the reaction mixture was filtered and evaporated to dryness to yield the product IVa as a pale brown oil which was used in the following reaction without further purification.

$^1$H NMR delta 1.6–2.2 (br m, 6H, —(CH$_2$)$_3$—) 2.18 (s, 3H, CH$_3$) 3.67 (br s, 4H, NH$_2$) 4.63 (m, 2H, CH) 6.4–6.8 (m, 7H, aromatic).

COMPOUNDS IV b-g

Similarly to the preparation of compound IVa, nitroethers IIIb-g were hydrogenated over Pd/C catalyst in ethyl acetate or ethanol. The amine products IVb-g were usually oils which darkened on exposure to air, gave the expected NMR spectra and were used without further purification.

COMPOUND Va

All the amine Va resulting from the reduction of IVa, assumed to be 5.58 mmol, 1,8-bis(dimethylamino)naphthalene (7.29 g, 34 mmol), NaI (0.45 g, 3 mmol) and methyl bromoacetate [reagent 11] (3.22 mL, 34 mmol) were refluxed in dry CH$_3$CN (75 mL) under N$_2$ for 16 h. The cooled reaction mixture was diluted with toluene (150 mL), filtered, washed with phosphate buffer pH 2 until washings were pH 2, and washed with H$_2$O. The organic layer was dried (MgSO$_4$) and evaporated to dryness to yield an oil, which was chromatographed on SiO$_2$ eluting with ethyl acetate-hexane to yield Va as a colorless oil (2.77 g, 85%).

$^1$H NMR delta 2.0 (br m, 6H, —(CH$_2$)$_3$—) 2.15 (s, 3H, Ar—CH$_3$), 3.61 (s, 12H —OCH$_3$), 4.13, 4.18 (2s, 8H, —CH$_2$—) 4.77 (m, 2H, CH), 6.5–6.8 (m, 7H, aromatic).

COMPOUNDS Vb-g

Similarly, amines IVb-g were alkylated with ethyl or methyl bromoacetate and after SiO$_2$ chromatography gave the expected products Vb-g as oil of which only one, Ve, crystallized (recrystallized from isopropyl ether M.p. 67°‒9°). Yields 30–80%.

$^1$H spectra were as expected; the shifts (ppm) of the ethane bridge protons were as follows: Vd, 4.50; Vc, 4.65; Vf, 4.77; Ve, 4.51; Vb, 4.80; Vg, 5.13.

COMPOUND VIa

Nitr-7 tetramethyl ester was prepared as follows:
TMSOTf (0.5 mL, 2.54 mmol) was added dropwise to a solution of Va (293 mg, 0.5 mmol), 6-nitropiperonal [reagent 12] (127 mg., 0.65 mmol) and 2,6-di-tert-butylpyridine (0.67 mL, 3 mmol) in dry CHCl$_3$, (3 mL) at room temperature under a N$_2$ atmosphere. (It is important for the CHCl$_3$ to be throughly dry; therefore fresh distillation from P$_2$O$_5$ is recommended.) After standing overnight, the reaction solution was diluted with CHCl$_3$ (10 mL) and poured into saturated aqueous NaHCO$_3$ (50 mL), separated and the aqueous extracted (2×15 mL) with CHCl$_3$. The combined extracts were washed with H$_2$O, dried (MgSO$_4$) and evaporated to dryness to yield the crude TMS-ether as a yellow oil. This was dissolved in CHCl$_3$, (25 mL) and tetrabutylammonium fluoride trihydrate (475 mg, 1.5 mmol) added in one portion. After 15 min. at room temperature, the solution was evaporated to dryness, dissolved in ethyl acetate:toluene (1:9 v/v, 100 mL), washed with H$_2$O (3×20 mL), dried (MgSO$_4$) and evaporated to yield the crude product as an orange oil. Separation by SiO$_2$ chromatography eluting with ethyl acetate-hexane gave VIa as a yellow, glassy foam. Yield 53%, M.p. 44°–9°.

$^1$H NMR delta 2.0 (br, m, 6H, —(CH$_2$)$_3$—), 2.18, 2.23 (2s 3H, Ar—CH$_3$), 3.58, 3.60, 3.62, 3.64 (4s, 12H, —OCH$_3$), 3.99, 4.02, 4.15 (3s, 8H, NCH$_2$—), 4.83 (br m, 2H, cyclopentane —CH—O), 6.03 (s, 2H, —OCH$_2$O—), 6.30 (d, 1H, —Ar$_2$CH—), 6.60–6.93 (m aromatic), 7.11 (s, 1H, piperonyl H-2), 7.28 (s, 1H, —OH), 7.37, 7.41 (2s, 1H, piperonyl H-5).

SAPONIFICATION OF ESTERS

Esters Va-g and VIa were dissolved in dioxane-methanol 1:1 and saponified by addition of an excess of 1M aqueous KOH, warming as necessary to aid dissolution. Reaction was complete within a few hours or after standing overnight. Usually, chelators were stored frozen in these diluted saponification mixtures. The free acids could be isolated by acidification and collection of the precipitate.

EXAMPLES

Specific properties of some of the compounds of the present invention are outlined in the following example. The example is for illustrative purposes only and is not intended to limit the scope of the claims in any way.

EXAMPLE I

This example illustrates that, from the teaching of the present invention, those skilled in the art can now predict changes in Ca$^{2+}$ affinity and Ca$^{2+}$:Mg$^{2+}$ selectively resulting from changes in the stereochemistry of the linkage between the two aromatic rings of the chelators.

As Table I shows, drastic changes in Ca$^{2+}$ affinity and Ca$^{2+}$:Mg$^{2+}$ selectivity can result from seemingly minor changes in the stereochemistry of the linkage between the two aromatic rings of the chelators. For example, in the cyclopentanediyl series, the cis-isomer (Va) has 300-fold higher affinity for Ca$^{2+}$ than the trans-isomer (Vb). By contrast, in the cyclohexanediyl series, the cis-isomer (Vc) has about 1.8-fold lower affinity for Ca$^{2+}$ and 1.7-fold higher affinity for Mg$^{2+}$ than the trans-isomer, but both are poorer than the unsubstituted parent chelator.

The magnitude and even the direction of these stereochemical effects was not predictable from prior art chelators. For example, in prior art analogs of ethylenediamine-N,N'-tetraacetic acid (EDTA) in which the central 1,2-ethanediyl linkage is substituted or replaced by rings, the cis-cyclopentanediyl analog is unknown, the trans-cyclopentanediyl analog has 3.7-fold higher affinity for Ca$^{2+}$ than the parent, the cis-cyclohexanediyl analog has 17-fold weaker Ca$^{2+}$ affinity than the parent, whereas the trans-cyclohexanediyl analog is 324-fold stronger than the parent (data from Martell and Smith, 1974). This pattern of response to substitution is strikingly different from our results in Table I.

Figure 2:
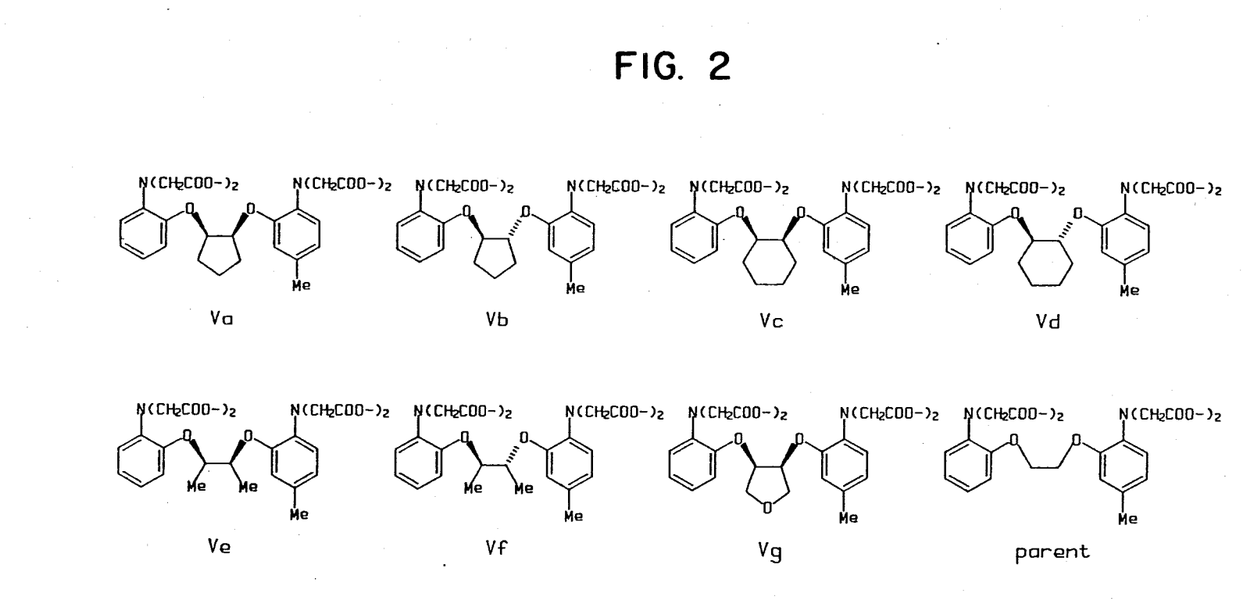
FIG. 2 is a chart showing the chemical formulas of precursor models (Va-g) of one type of chelator of the present invention. The chart also shows the formula of a known compound having the "parent" linkage as shown below.

The data from Table I can be explained and used to predict affinities for other compounds by constructing space-filling molecular models of the chelators. Stronger affinities for Ca$^{2+}$ are associated with conformations in which the distance between the ether oxygens is minimized and in which the lone pairs of the two amino nitrogens and two ether oxygens can all point into a central cavity. Structures such as (Va) (Vg) and (VIIa) which tend to form such favorable conformations give the highest $Ca^{2+}$ affinities, whereas flexible structures such as the parent and Vf give intermediate affinities, and structures for which such conformations are excluded give the lowest affinities (Vb, Vc, Vd). Therefore by construction of physical or computer molecular models and consideration of the above rules for steric relations of the ether oxygens and amino nitrogens, the cation affinities can be predicted.

The effects of adding substituents on the benzene rings meta or para to the amino groups are also quite predictable, not on the basis of stereochemistry but instead by linear free-energy relationships. Electron-donating and withdrawing groups respectively raise and lower the cation affinities in a semiquantitatively predictable manner without significant steric effects. Thus the $Ca^{2+}$ affinities of the nitrobenzhydrols VII containing one nitrobenzyl substituent are 2–2.5 fold lower than their precursors V, and the effect of photoisomerization to VIII is to reduce affinities a further 40–60 fold. Specifically, nitr-7(VIIa) has a dissociation constant for $Ca^{2+}$ of 53 nanomolar at 22° C., 0.1M ionic strength. Rejection of $Mg^{2+}$ is excellent ($>10^5$), the dissociation constant for $Mg^{2+}$ being 5.7 millimolar. Upon photolysis to the nitrosobenzophenone VIII, the dissociation constant for $Ca^{2+}$ increases to 3 micromolar. Release of $Ca^{2+}$ is quite fast, occurring with an exponential time constant of 1.8 millisecond after a submillisecond light flash.

Addition of nitrobenzyl substituents to both benzene rings (see Brief Description of the Invention) would reduce $Ca^{2+}$ affinities 4–6 fold from the precursors V, and photolysis of both nitrobenzyl substituents would then reduce affinities a further 1600–3600 fold.

TABLE I

| | Chelator V | | | |
|---|---|---|---|---|
| | Formula Linkage | | | After Saponification | |
| FIG. 2 Notation | Notation | | Conformation of Linkage | $K_d$ for $Ca^{2+}$ (in nanoMolar) | $K_d$ for $Mg^{2+}$ (in milliMolar) |
| | $R^8$ | $R^9$ | | | |
| Va | cis-$(CH_2)_3$— | | See FIG. 2 | 20 | 4.2 |
| Vb | trans-$(CH_2)_3$— | | See FIG. 2 | 6000 | <100 |
| Vc | cis-$(CH_2)_4$— | | See FIG. 2 | 400 | 5.9 |
| Vd | trans-$(CH_2)_4$— | | See FIG. 2 | 220 | 10 |
| Ve | cis-Me | Me | See FIG. 2 | 1000 | 7.8 |
| Vf | trans-Me | Me | See FIG. 2 | 102 | 8.9 |
| Vg | cis-$CH_2OCH_2$— | | See FIG. 2 | 50 | 7.2 |
| (parent) | H | H | See FIG. 2 | 79 | 8.1 |

SUMMARY

Thus it can be seen that the present invention discloses a new class of photolabile $Ca^{2+}$ chelators which store $Ca^{2+}$ in a physiologically inactive form until illuminated with ultraviolet light, whereupon the $Ca^{2+}$ tends to be released. This released $Ca^{2+}$ is then free to activate physiological processes. Since the new class of chelators disclosed herein extend the ability to use light to control the release of $Ca^{2+}$ inside cells they will be extremely useful to biological researchers trying to study the many cellular functions which calcium is now believed to control. Such functions include ion-gating and muscle contraction.

Various modifications of the invention in addition to those shown and described herein will become apparent to those skilled in the art from the foregoing description and accompanying drawings. Such modifications are intended to fall within the scope of the appended claims.

What is claimed is:

1. A chemical compound having the general formula:

and the pharmaceutically acceptable non-toxic salts and esters thereof wherein:

A is —$NO_2$ or —H;

$R^1$ is selected from the group consisting of —H (unless $R^2$ is also H), —$CH_3$, —F, —Cl, Br, alkyl, —$C_1$–$C_4$ alkoxy, and $NHR^6$ $R^2$ is selected from the group consisting of —H (unless $R^1$ is also H), —$CH_3$, —F, —Cl, —Br, and $C_1$–$C_4$ alkoxy;

$R^3$, $R^4$ and $R^5$ are independently —H, OH, $NR^6R^7$, or alkoxy, or $R^3$ and $R^4$ together are —$OCH_2O$— or —$OCH_2CH_2O$— and $R^5$ is —H, OH, $NR^6R^7$, or alkoxy, or $R^4$ and $R^5$ together are —$OCH_2O$— or $OCH_2CH_2O$— and $R^3$ is —H, OH, $NR^6R^7$, or alkoxy;

X is selected from the group consisting of —OH, alkoxy, —Cl, —Br, —$NR^6R^7$, —$OCOCH_3$, —$OCOCF_3$, —$OCOCH_2NH_2$, —$OPO_3H$, and —O—$SO_2CH_3$;

$R^6$ and $R^7$ are independently —H, methyl or ethyl; and $R^8$ and $R^9$ are independently —H, $CH_3$, —$C_2H_5$, or —$CH_2OH$ except that both may not be —H simultaneously; or $R^8$ and $R^9$ together are —$(CH_2)_m$—Y—$(CH_2)_n$—wherein m and n are independently 1 or 2 and Y is selected from the group consisting of —$CH_2$—, —O—, —$NR^6$—, —S—, and —S—S—; and

W is —H, —OH, or —$NHR^6$.

2. The compound of claim 1 wherein the 2-bis(carboxymethyl)amines are alpha-acyloxyalkyl esters.

3. The compound of claim 2 wherein said alpha-acyloxyalkyl esters are acetoxymethyl esters.

4. The compound of claim 1 wherein $R^2$ is methyl.

5. A chemical compound having the general formula:

and the pharmaceutically acceptable non-toxic salts and esters thereof wherein:

A is $-NO_2$ or $-H$;

$R^1$ is selected from the group consisting of $-H$, $-OH$, $-CH_3$, $-F$, $-Cl$, $-Br$, alkyl, $C_1-C_4$ alkoxy, and $-NHR^6$;

$R^3$, $R^4$ and $R^5$ are independently $-H$, OH, $NR^6R^7$, or alkoxy, or $R^3$ and $R^4$ together are $-OCH_2O-$ or $-OCH_2CH_2O-$ and $R^5$ is $-H$, OH, $NR^6R^7$, or alkoxy, or $R^4$ and $R^5$ together are $-OCH_2O-$ or $-OCH_2CH_2O-$ and $R^3$ is $-H$, OH, $NR^6R^7$, or alkoxy;

X is selected from the group consisting of $-OH$, alkoxy, $-Cl$, $-Br$, $-NR^6R^7$, $-OCOCH_3$, $-OCOCF_3$, $-OCOCH_2NH_2$, $-OPO_3H$, and $-OSO_2CH_3$;

$R^6$ and $R^7$ are independently $-H$, methyl, or ethyl; and $R^8$ and $R^9$ are independently $-H$, $CH_3$, $-C_2H_5$, or $-CH_2OH$ except that both may not be $-H$ simultaneously; or $R^8$ and $R^9$ together are $-(CH_2)_m-Y-(CH_2)_n$ where m and n are independently 1 or 2 and Y is selected from the group consisting of $-CH_2-$, $-O-$, $NR^6$, $-S-$, and $-S-S-$; and W is $-H$, $-OH$ or $-NHR^6$.

6. The compound of claim 5 wherein the 2-bis(carboxymethyl)amines are alpha-acyloxyalkyl esters.

7. The compound of claim 6 wherein said alpha-acyloxyalkyl esters are acetoxymethyl esters.

8. The compound cis-1-(2-bis(carboxymethyl)amino-5-(1-hydroxy-1-(2-nitro-4,5-methylenedioxyphenyl)methyl)phenoxy)-2-(2-bis(carboxymethyl)amino-5-methylphenoxy)cyclopentane.

* * * * *

UNITED STATES PATENT AND TRADEMARK OFFICE
CERTIFICATE OF CORRECTION

PATENT NO.   : 4,806,604
DATED        : February 21, 1989
INVENTOR(S)  : Roger Tsien, et al.

It is certified that error appears in the above-identified patent and that said Letters Patent is hereby corrected as shown below:

Column 1, line 33, "uphotolyzed" should be --unphotolyzed--.

Column 3, line 42, "tetracarbxylate" should be --tetracarboxylate--.

Column 5, line 33, after "$(CH_2)_n$-", the phrase "where m and n are independently" should not be italicized.

Column 9, line 45, "1h" should be --1H--.

Column 9, line 45, delete "H-49" and insert therefor --H-4)--.

Column 10, line 37, "delta 16-2.1" should be --delta 1.6-2.1--.

Column 13, Table I, line 44, delete "<100" and insert therefor -->100--.

Signed and Sealed this

Tenth Day of April, 1990

Attest:

HARRY F. MANBECK, JR.

*Attesting Officer*       *Commissioner of Patents and Trademarks*